United States Patent
Santoro et al.

(10) Patent No.: US 6,440,454 B1
(45) Date of Patent: Aug. 27, 2002

(54) MATRIX-TYPE TRANSDERMAL PATCH FOR STEROID HORMONES

(75) Inventors: Antonino Santoro; Lucio C. Rovati, both of Monza (IT)

(73) Assignee: Rottapharm BV, Amsterdam (NL)

( * ) Notice: Subject to any disclaimer, the term of this patent is extended or adjusted under 35 U.S.C. 154(b) by 0 days.

(21) Appl. No.: 09/720,324

(22) PCT Filed: Jun. 22, 1999

(86) PCT No.: PCT/EP99/04305
§ 371 (c)(1),
(2), (4) Date: Apr. 9, 2001

(87) PCT Pub. No.: WO99/66908
PCT Pub. Date: Dec. 29, 1999

(30) Foreign Application Priority Data

Jun. 22, 1998 (DE) .......................... 198 27 732

(51) Int. Cl.⁷ .................. A61F 13/00; A61F 13/02; A61K 9/70; A01N 25/34; A61L 15/16
(52) U.S. Cl. .................. 424/449; 424/402; 424/443; 424/447; 424/448; 424/484
(58) Field of Search .................. 424/402, 443, 424/447, 449, 484, 448

(56) References Cited

U.S. PATENT DOCUMENTS

| | | | | |
|---|---|---|---|---|
| 4,559,222 A | * | 12/1985 | Enscore et al. | 424/28 |
| 5,252,334 A | * | 10/1993 | Chiang et al. | 424/448 |
| 5,989,586 A | * | 11/1999 | Hsu et al. | 424/449 |
| 6,153,216 A | * | 11/2000 | Cordes et al. | 424/449 |

FOREIGN PATENT DOCUMENTS

DE   WO 97/23227   *   7/1997   .................. 424/449

* cited by examiner

Primary Examiner—Thurman K. Page
Assistant Examiner—Humera N. Sheikh
(74) Attorney, Agent, or Firm—Frommer Lawrence & Haug LLP; Ronald R. Santucci

(57) ABSTRACT

The present invention refers to a transdermal patch for the release of Estradiol and at least one progestogen agent through the skin, comprising or consisting of an outer backing foil, a matrix and a protective liner wherein a) the Estradiol and the progestogen agent(s) are present in the matrix in an oversaturated solution, b) the matrix contains 1 to 5 wt% activated $SiO_2$, and c) the matrix has a moisture content of less than 0.7 wt.-%. The patch can be used for hormonal replacement therapy.

29 Claims, 4 Drawing Sheets

MATRIX-TYPE TRANSDERMAL PATCH FOR STEROID HORMONES

The present invention relates to a Transdermal Drug Delivery System (TDDS) (a transdermal patch), to a method for manufacturing such system, and to the use of such system for hormone replacement therapy.

Estrogens are hormones which are necessary for the sexual development of females at puberty and for the maintenance of the oestrous cycle and secondary sexual characteristics. Estrogens and progesterone induce changes in the reproductive tract and elsewhere in the body of females during the menstrual cycle. Blood estrogen concentrations must be above a certain level for the maintenance of both proliferate and (together with progesterone) secretory phases of the uterine endothelium.

The menopause occurs when menstruation ceases and indicates the end of a woman's reproductive life; during this phase of a woman's life there is a progressive loss of ovarian functions and there is a decrease in the production of Estradiol and other hormones.

About 40% of women develop menopausal symptoms serious enough to require medical treatment; the symptoms include mainly vasomotor instability (hot flushes and sweating) and mood and sleep disturbances; during menopause, there is a gradual decrease of bone mass due to a loss of the modulating effect of Estradiol on bone resorption and this process normally leads to osteoporosis. The loss of estrogenic activity changes also the lipid metabolism with a decrease of the ratio of high density lipoprotein (HDL) to low-density lipoprotein (LDL), and this change increases the risk of cardiovascular diseases.

All these negative effects that can occur in a woman in menopause can be eliminated or at least reduced by an appropriate replacement therapy with estrogen agents, i.e. by the "Hormonal Replacement Therapy" (HRT).

Oral administration of estrogens as HRT has been extensively used for about 30 years and it was confirmed that, besides the climacteric symptoms, HRT was effective in reducing the death by cardiovascular diseases.

However, although oral estrogens are effective as HRT, related adverse effects are a problem; a high amount (60–90%) of the oral estrogens are converted within the gut wall and liver to inactive metabolites having hepatic adverse effects, therefore relatively high doses of oral estrogens are required to compensate sate first-pass metabolism.

Several non-oral formulations of estrogens, which avoid hepatic first-pass effects, have been developed and used as HRT; they include subcutaneous implants, intramuscular injections, vaginal creams and percutaneous gels. However, with such preparations, control of dosage is difficult and patients compliance is poor.

More recently, transdermal preparations delivering Estradiol at a constant rate have become available. In women with an intact uterus estrogens produce hypertrophy of the endometrium which could provoke cancer. In order to minimize the risk of endometrial hyperplasia and carcinoma of the estrogen therapy in women with an intact uterus the treatment must be opposed intermittently by a progestogen to be associated to the estrogen. The opposition therapy normally is carried out by oral administration of a progestogen like medroxyprogesterone acetate, norethindrone, norethindrone acetate, progesterone, etc. for 10–14 days per month.

A patch delivering both Estradiol and a progestogen is an useful alternative to a method which combines the transdermal administration of Estradiol with the daily oral administration of progestogen. Compliance is likely to be further improved and side effects minimized thanks to a lower progestogen dosage requirement compared with oral therapy.

Several problems, however, are encountered when including a progestogen in a transdermal patch. Among these one important obstacle is the low, therapeutically uneffective drug release obtained with a transdermal patch of relatively small size; this is due to the poor skin permeation properties of steroid hormones. Another obstacle is the low stability of some progestogens that leads to degradation products.

In the light of the aforementioned art, there is a need for an optimal transdermal drug delivery system releasing Estradiol and a progestogen through an intact skin resulting in a constant systemic absorption rate.

Numerous patents refer to the delivery of steroid hormones to the systemic circulation via a transdermal route, and some of them refer to transdermal systems containing Estradiol and Norethindrone Acetate.

Some inventions refer to the discovery of special matrix formulations containing substances able to reduce the re-crystallization of Estradiol and Norethindrone. Indeed, it is well known for scientists skilled in TDDS that, in order to obtain an adequate release of steroid hormones from transdermal patches, it is necessary to reach in the matrix high concentrations of the hormones (high drug load) or to significantly increase the release area of the patch. The first solution, however, leads quite often to re-crystallization of the hormones during the shelf-life of the product with consequent reduction of the drug release; the second solution often is not acceptable since it reduces patient compliance because of the size of the patch and even could have a negative effect on the adhesivity of the patch during the intended period of use of the product.

A third possibility to reach an adequate flux from matrix transdermal patches is the inclusion of absorption enhancers (penetration enhancers) in the matrix formulation to generate a high flux of the active compounds when the system is applied to the skin. Typical known enhancers are ethanol, glycerolmonolaurate, DMF, polyethylenglycole monolaurate, etc. Absorption enhancers, however, provoke skin reactions and systemic side effects and this aspect reduces the ratio efficacy/tolerability of the resulting transdermal systems. They increase the permeability of the stratum corneum of the skin through a modification of the cellular layer, provoking lesions of the skin; they can moreover be absorbed by the skin provoking systemic side effects.

Another problem known by skilled researchers in TDDS formulations is the low stability of Norethindrone Acetate in acrylic based formulations that leads to degradation products.

WO 96/03119 (PCT/EP 95/02938) relates to a device for the administration ministration of Estradiol alone or in combination with progestogen(s), encompassing a specific penetration enhancer that achieves elevated transdermal fluxes and optionally an anti-oxidant that achieves good product stability; however, as mentioned above, penetration enhancers can provoke skin reactions.

WO 94/23707 (PCT EP 94/01231) describes an active substance containing laminated plasters with a carrier and a matrix made of one or two polymers, as well as Vitamin E (tocoferol); tocoferol, however, is not free of potential skin reactions in an occlusive patch that has to remain attached to patient skin for 3–4 days.

U.S. Pat. No. 4,379,454 refers to a transdermal liquid reservoir patch which contains Estradiol in an alcoholic gel solution; the alcohol contained in the reservoir, however, acts also as an absorption enhancer and can provoke skin reactions.

WO 9740792 A discloses a matrix type patch for transdermally administering ministering a steroid hormone which comprises a skin permeation enhancing amount of a diethanolamide of a 12–18 C fatty acid.

WO 95/09618 (PCT/EP 94/03269) describes the use of octyldodecanol as crystallization inhibitor in matrix patches containing Estradiol and Norethindrone Acetate.

DE 44 29 664 refers to a transdermal therapeutic system containing Estradiol and a water absorbing additiv, which is part of the matrix. The system according to this document does not contain a progestogen agent and is said to be applicable to Estradiol only.

A system for the application of norethisterone acetate is disclosed in DE 195 48 332. It is, however, stated in this document that the addition of an Aerosil to a matrix does not result in a reduced formation of degradation products of norethisterone acetate.

The object of the invention is the development of a TDDS for HRT releasing Estradiol and at least one progestogen with improved skin permeation of the hormones compared to prior art.

Figure 1:
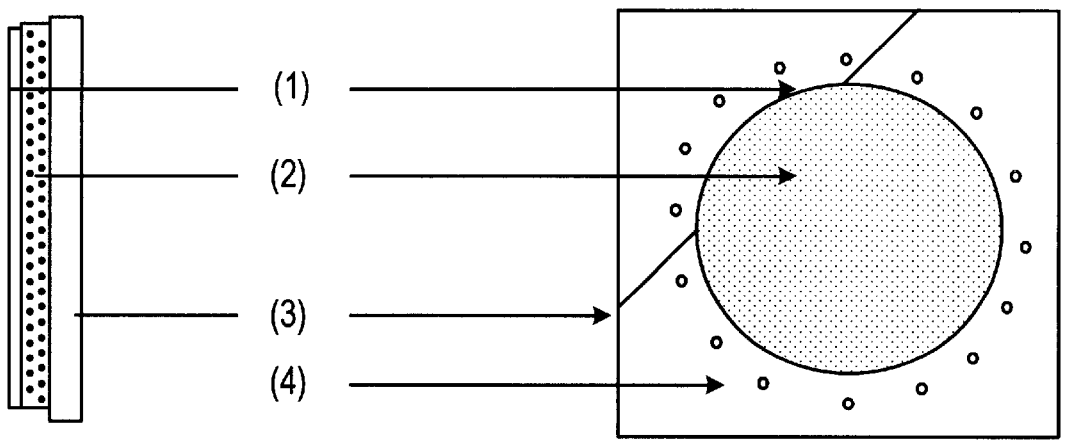
"FIG. 1" represents a not-to-scale cross-sectional view and a front view of the transdermal patch.

At the same time the TDDS is to have the following characteristics:

very simple composition and structure;
absence of skin penetration enhancers or other compounds which can irritate the skin;
prolonged and controlled rate of release of the hormones up to 7-days;
small size;
good adhesivity onto the skin during the intended period of use;
easy removal from the skin at the end of the treatment;
"skin-safe" pressure sensitive adhesive;
absence of re-crystallization of Estradiol and of the progestogen;
stability of Estradiol and Norethindrone Acetate without degradation products;
transparent, cosmetically attractive system;
good physical stability, i.e. small tendency of creeping of the matrix so that the system can easily be removed from the package.

It has now been found that it is possible to obtain a TDDS containing steroid hormones that can release high amounts of hormones from relatively small matrix areas without the use of penetration enhancers and avoiding the re-crystallization and the degradation of the hormones in the matrix and satisfying all the above characteristics.

Thus the present invention provides a transdermal patch for the release of Estradiol and at least one progestogen agent through the skin, comprising or consisting of an outer backing foil, a matrix and a protective liner wherein the Estradiol and the progestogen agent(s) are present in the matrix in an over saturated solution, the matrix contains 1 to 5, preferably 1 to 4 wt-% activated $SiO_2$ and the matrix has a moisture content of less than 0.7 wt.-%. Preferably the matrix has a moisture content of less than 0.5 wt-% and especially preferred is a moisture content of less than 0.4 wt-%. The moisture content refers to the content of free water, that is, the water not adsorbed on or absorbed in the $SiO_2$.

In the description and in the claims all percentages refer to weight-% if not indicated otherwise and all contents of the matrix, given in percentages, refer to the weight of the final matrix in the patch, that is, the matrix which comprises the copolymer(s), estradiol, the progestogen agent(s) and optionally further compounds.

Surprisingly it was found that the hormone release rate from such "moisture-free" matrix-type TDDS containing activated $SiO_2$ increases significantly with reference to the same non moisture free matrix without using penetration enhancers:

It was found that moisture-free semi-solid matrix-type TDDS which contain ativated silicon dioxide and steroid hormones in over-saturated solutions have an optimal performance with reference to the release rates of such steroid hormones when applied to human skin. Such unexpected behaviour, although not known with certainty and without intention to be bound to any specific mechanism, is believed to be due to absorption of water from the skin, especially by activated silicon dioxide, when such moisture-free activated silicon dioxide containing systems are applied to human skin and to the consequent decrease of the solubility of the hormones in the matrix. This provokes an increase of the driving force in the system and therefore results in a better flux of the drugs (such surprising characteristics of a matrix containing non water-soluble polymers were not known). It is therefore possible to have a high release of the hormones with TDDS of small release areas (and/or reduced concentration of hormones).

Moisture-free matrix systems can be obtained by standard manufacturing TDDS processes and concomitant or subsequent treatment of the systems with infrared rays. Thus the energy of water molecules is activated provoking the evaporation of residual water from the matrix at relatively low temperatures that do not provoke degradation of the steroid hormones.

Moisture-free matrix TDDS which contain activated silicon dioxide in the matrix show an enhanced drug release into the skin. Such surprising indirect enhancing properties in TDDS of moisture-free matrix TDDS containing activated silicon dioxide for steroid hormones were not previously known. In this invention the high rate of delivery is due to a different mechanism compared to that of penetration enhancers utilized in TDDS:

It is assumed that activated $SiO_2$ enhances the flux of water from the skin into the matrix thereby increasing the force which drives the hormones out of the matrix so that the flux of Estradiol and the progestogen agent(s) into the skin is/are increased.

It has been found that a preferred amount of $SiO_2$ in the matrix lies in the range from 2.5 to 3.5 wt-%; and an amount of about 3 wt-% $SiO_2$ is especially preferred. An amount above 5 wt-% is detrimental to the flux of the active ingredients in the matrix in that the concentration of the ingredients in the matrix must be lowered when the content of $SiO_2$ is increased. An amount of less than 1 wt-% $SiO_2$ will not attract a sufficient amount of water to increase the flux of the active ingredients.

$SiO_2$ can be activated according to the present invention by irradiating the patch—with or preferably without the release liner being applied—with an IR-source. At the same time irradiation of the matrix reduces its water content to the required level.

The matrix systems according to the present invention can thus be obtained by standard manufacturing TDDS processes and concomitant or subsequent treatment of the systems with infrared rays.

By irradiation the energy of water molecules is probably activated provoking the evaporation of residual water from the matrix and inter alia the evaporation of absorbed water of $SiO_2$ at relatively low temperatures.

Activated silicon dioxide can be prepared by irradiating silicon dioxide (like an Aerosil, especially Aerosil 380) with an IR source.

It has been shown that the results are particularly adequate when irradiating the matrix of the patch including the silicon dioxide with infrared rays having a wavelength of 1 to 100 $\mu$m, preferably of 1 and 10 $\mu$m, for 1 to 10 minutes, preferably for 1 to 5 minutes with an incandescent filament lamp of an adequate power (Watt) at a distance of 20 to 40 cm generating a temperature of 40 to 120° C., preferably of 60 to 90° C. Preferably the lamp(s) have an active power of 100 to 3000 Watt.

The inclusion in the matrix of activated, preferably colloidal, silicon dioxide moreover contributes to maintain the system anhydrous. This condition of the matrix system probably reduces the solubility of the hormones in the patch and increases the flux.

The most important feature of this invention is the use of a moisture-free matrix containing activated silicon dioxide which allows for a high flux of drugs into the skin from small patches without skin penetration (rate) enhancers.

The at least one pressure sensitive adhesive used for the matrix of this invention is selected from a group of vinylacetate containing acrylate copolymers; specifically the matrix consists of one, two or more pressure sensitive adhesive copolymers, obtainable by the radical copolymerisation of:

a) 2-ethylhexylacrylate (2-EHA) preferably in an amount of 44% to 80%, preferably 48% to 75% and especially 50% to 68%.

b) Hydroxyethyl-acrylate (HEA) preferably in an amount of 2.5% and 9.7%, preferably 4.0% to 5.0%;

c) vinylacetate (VA) preferably in an amount of 8% to 48.2%, preferably 20% to 26%;

d) glycidylmethacylate (GMA), preferably in an amount of 0.01 to 0.3%, preferably of 0.1% to 0.2%;

e) and in the presence of other substances in quantities of up to 5%, all percentages being based on the weight of the matrix of the final patch.

Among several progestogens, Norethindrone Acetate is preferred because it is effective at low doses and therefore can be formulated in TDDS and because it has some additional effects, e.g. on libido, that are absent in other progestogens like progesterone and medroxyprogesterone.

In the described matrix Estradiol (as hemihydrate) and the progestogen agent(s) like Norethindrone Acetate can be maintained in high concentration. Thus the matrix can have an Estradiol content of 1.0 to 3%, preferably of 1.5 to 2.5% and especially of 1,8 to 2.4% and a content of at least one progestogen agent like Norethindrone Acetate of 2 to 12%, preferably of 4 to 11% and especially of 5 to 9%. In these concentrations, Estradiol and the progestogen agent like Norethindrone Acetate, although being in a supersaturated (=over saturated) solid solution in this matrix, do not re-crystallize and are maintained in a condition that confers to the steroid hormones a high thermodynamic activity.

The matrix can preferably contain 1 to 5 wt-% of silicon dioxide to contribute to the maintenance of an anhydrous state in the matrix and to provoke absorption of water from the skin when the patch is applied.

In order to eventually improve the matrix characteristics, it is possible to include in the matrix small amounts of up to 4%, preferably of up to 3% of other compounds having e.g. a solubilizing effect on the active ingredients, or avoiding re-crystallization thereof or having drying activities or acting as preservatives or antioxidants, etc.

Preferably the thickness of the matrix should be kept low enough so that it can be dried during the drying step of the manufacturing process and that the solvent content, including the moisture content can be reduced to a minimum.

Thus the matrix preferably has a thickness of 20 to 100 $\mu$m, more preferred of 30 (or 40) to 80 $\mu$m and especially of 50 to 70 $\mu$m.

The patch according to the present invention can be a laminated composite with a backing foil that is substantially impermeable to the drugs and the adhesive copolymer(s) of the matrix and supports the matrix.

The backing foil can be made from one or more materials selected from the group consisting of polyester, polyurethane, polyethylene, polyethylene terephtalate, polypropylene and polyvinyl chloride materials; and the side of the backing foil not facing the matrix can be lacquered, preferably by a lacquer comprising epoxy resins or polyaminoamido resins containing opacifying agents and it can have a thickness of 10 to 45 (or 50) $\mu$m and preferably 12 (or 15) to 30 $\mu$m.

Thus the backing foil or layer according to the present invention can be an occlusive or a transparent material, preferably a transparent polyester material such as polyethylene terephthalate.

For better handling during its production such material can be lacquered on the side not in contact with the matrix with an epoxy resin containing opacifying agents.

In order to protect the matrix during storage a protective (release) liner is used; such release liner can be impermeable to the active ingredients and the pressure sensitive adhesive (s) and should be easily removable by the patient before the application of the patch.

The release liner can be made of at least one foil of paper, polyester, polyethylene, polypropylene, polyethylene terephtalate (PET) or polyvinylchloride. It is preferably coated, to reach the requested release strength, on one or both sides with a silicon system or fluoropolymer coating blend. The optimum thickness for an appropriate rigidity of the release liner is 50 to 150 (or 200) $\mu$m and preferably between 60 (or 80) to 120 (or 150) $\mu$m.

In order to facilitate its detachment from the patch, a pull-off tag can be cut in the release liner and, where requested, an appropriate profile ring is stamped on the liner in order to maintain a distance from the backing foil to the internal wall of a pouch (sachet) material into which the patch can be sealed, so that the profile ring prevents the sticking of the patch on the internal wall of the sachets. The sachet can comprise a humidity impermeable foil, preferably a multi-layered foil, which is preferably made of sheets of aluminium, paper, polyethylene or polyvinylchloride, especially Surlyn$^R$.

To maintain the matrix "moisture-free" (to allow a high flux of the hormones) the sachets can contain as a precaution a desiccant such as silica gel, sodium sulfate, calcium sulfate, calcium carbonate dihydrate or a mixture thereof.

Preferably the transdermal patch according to the invention has a circular or oval shape or a square shape with round edges, and/or a release area of 5 to 60 cm² and preferably 8 to 40 cm².

According to the present invention there is also disclosed the use of a transdermal patch according to the invention for hormonal replacement therapy.

EXAMPLES

The description of the present invention and the manufacture of the relevant TDDS delivering Estradiol and a progestogen agent like Norethindrone Acetate are illustrated by the following examples:

Example 1
Preparation of the Adhesive Mixture with Ingredients 12.05 kg of a vinylacetate-acrylate copolymer solution having a solid content of about 51% are homogenized under stirring together with 0.1621 kg of Estradiol Hemihydrate and 0.6055 kg of Norethindrone Acetate; the suspension is transferred into 6.96 kg of a 50:50 mixture of Ethyl Acetate and Ethanol (these solvent materials were later removed during drying) and 0.2098 kg of Aerosil 380 are added; the mixture is then maintained under stirring for 24 hours at room temperature until a homogenous mass is obtained.

The ratio of the monomers used to prepare the vinylacetate-acrylate copolymer of the (final) matrix obtained are as follows:

2-ethylhexyl acrylate: 58.67% vinylacetate: 22.43%

2-hydroxyethylacrilate: 4.31% glycidyl metacrylate: 0.13%

Preparation of the Medicated Laminate

The drug solvent polymer mixture was then cast to a thickness of about 60 micrometers on a polyester film (backing foil) to obtain after drying a matrix having a weight of 60 g/m².

Drying of the medicated laminate is carried out at a temperature between 35 and 95° C. and this leads to a composition of 0.135 mg of Estradiol and 0.520 mg of Norethindrone Acetate per cm² of the dried matrix.

At this temperature the matrix cannot be dried completely and the water content deriving from the materials and solvents used, from the environment and also from the Estradiol Hemihydrate used cannot be eliminated. The medicated laminate, after drying, is treated for about 2 minutes with an IR lamp able to eliminate the water and to activate the silicon dioxide at a temperature of less than 100° C. In this way it is possible to avoid degradation of the hormones and especially of Norethindrone Acetate that can occur if the matrix is treated at high temperatures.

After drying and IR lamp treatment, the release liner, i.e. a polyester foil of 80 μm thickness, coated with a fluoropolymer, is stuck on the matrix to form the final medicated laminate.

Punching of the Transdermal Patch

Circular or oval shapes or square shapes with round edges having a release area of 8 to 40 cm² are punched from the medicated foil to form the final transdermal patches; the size is decided according to the requested release rate of Estradiol and Norethindrone Acetate.

A not-to-scale cross-sectional view and a front view of a transdermal patch obtained according to this invention is given in FIG. 1.

In FIG. 1
- (1) is a lacquered backing foil
- (2) is a drug containing adhesive matrix
- (3) is a protective liner, and
- (4) is a profile ring.

Sealing into the Pouches

Each transdermal patch is sealed into a pouch not permeable to moisture and composed of a 4-layered material made by paper, polyethylene foil, aluminium foil and surlyn ionomer foil. To maintain the matrix of the TDDS moisture-free, a desiccant like calcium carbonate dihydrate may be included in the pouch.

Comparative Example 2
(Reference Preparation)

Preparation of the Medicated Laminate

Proceed as in Example 1.

All the remaining steps are as in Example 1; in this example, however, the medicated laminate is not irradiated with the infrared lamp(s).

Quantitative Assay of (Free) Water in Transdermal Patches

Figure 2:
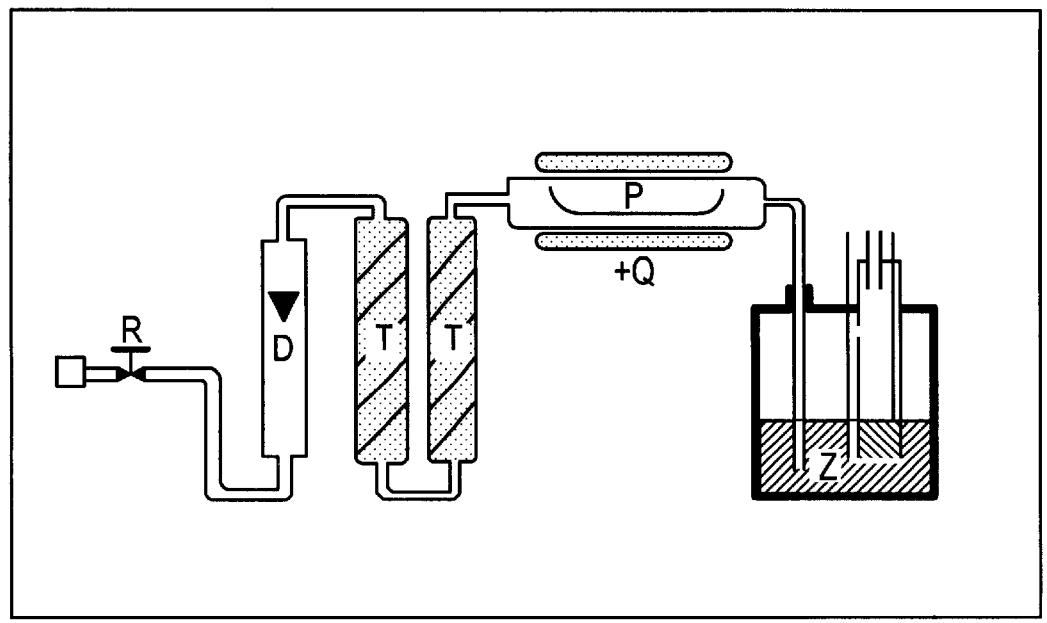
"FIG. 2" demonstrates a Karl-Fischer titration cell where titration is carried out by a Coulometric method.

The transdermal patches resulting from each of the preparations described have been tested with the Karl-Fischer method in order to quantify the (free) water content in the matrix of the systems:

The (free) water content in the transdermal patches can be driven off in a tube furnace at a certain temperature. It can then be transferred to a Karl-Fischer titration cell by an inert gas where it is titrated by a Coulometric method with specific reagents. A suitable arrangement for such a technique is depicted in FIG. 2.

A constant flow of air is achieved by regulating valve R and monitoring the air flow using the flowmeter D. The air is then dried in the drying towers T before being passed over the heated sample (P) (a patch or portion of patch) into the titration cell Z depicted in FIG. 3.

Figure 3:
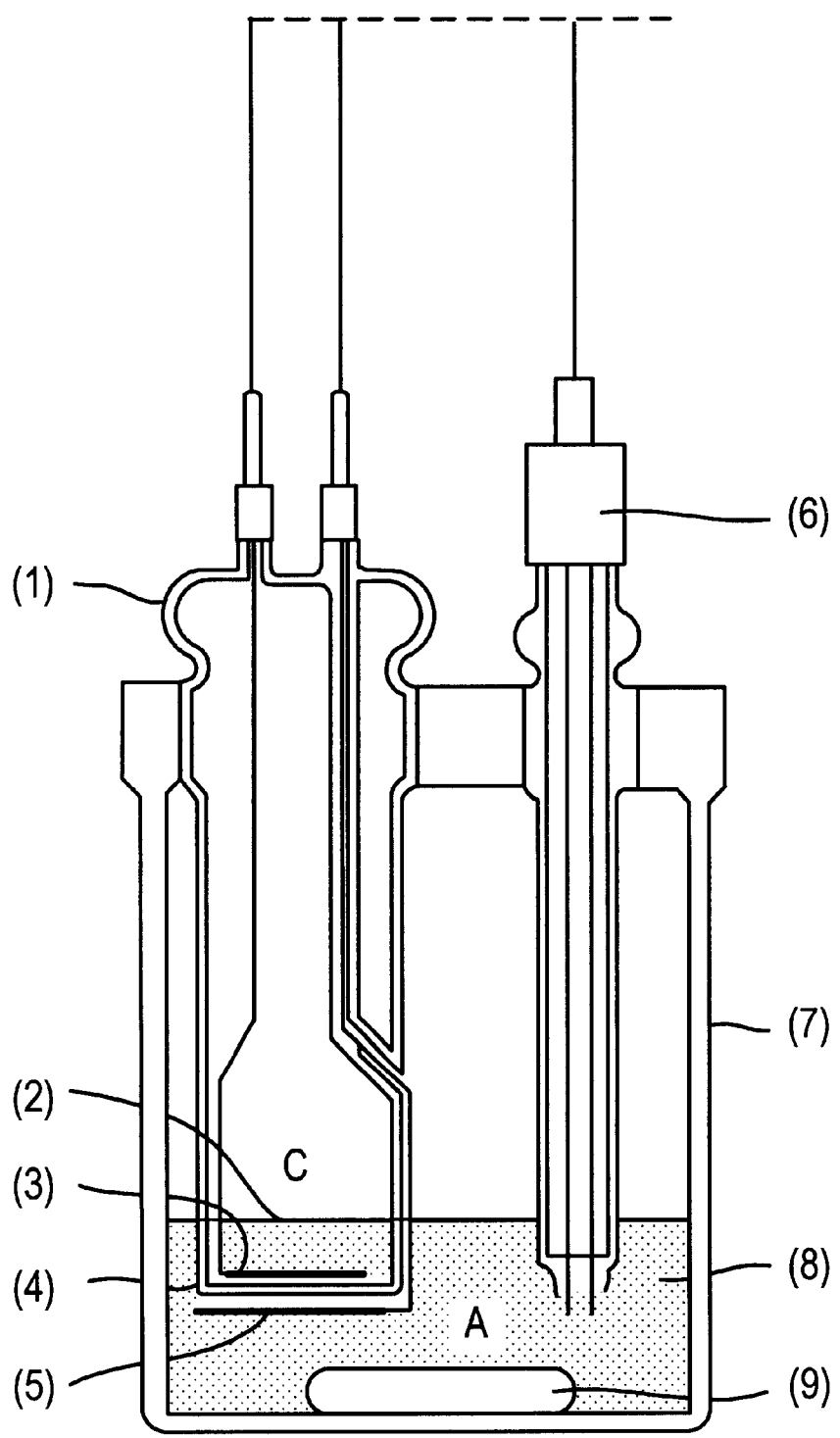
"FIG. 3" demonstrates a titration cell.
Figure 4:
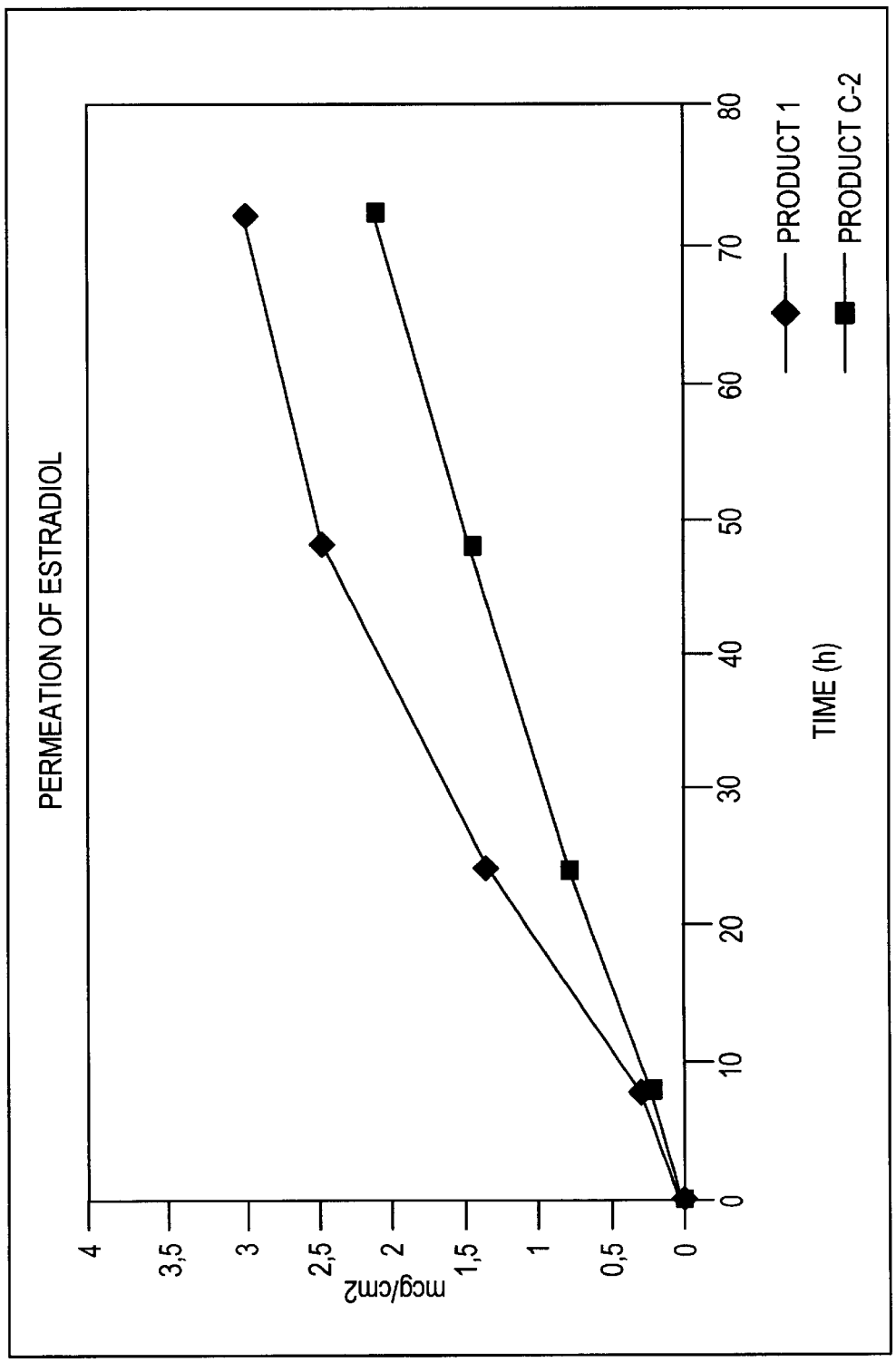
"FIG. 4" represents a graph of the flux of estradiol obtained from the TDDS.
Figure 5:
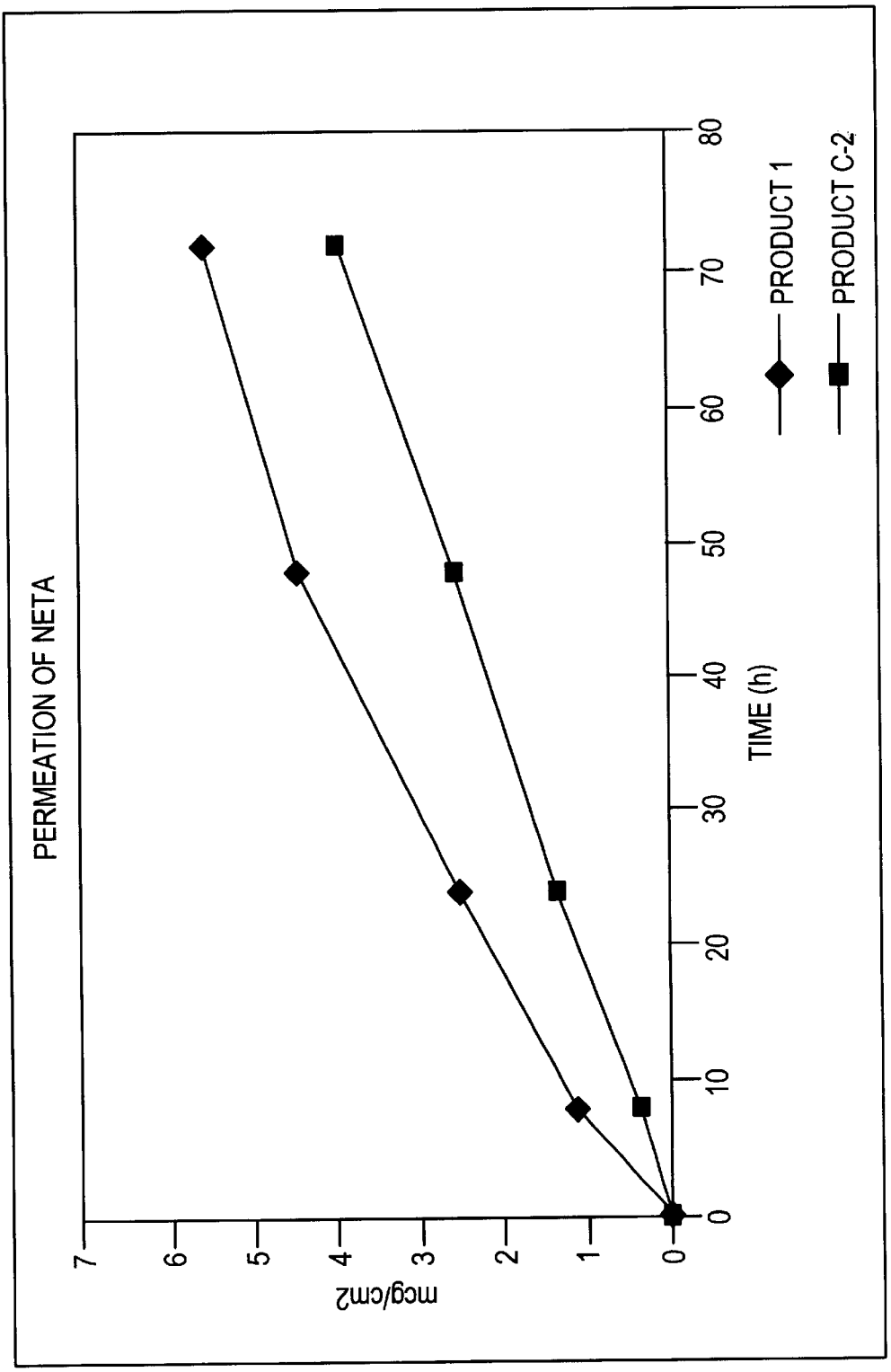
"FIG. 5" represents a graph of the flux of NETA obtained from the TDDS.

In FIG. 3
- (1) is an inner burette,
- (2) is a catholyte,
- (3) is a cathode,
- (4) is a membrane,
- (5) is an anode,
- (6) is a detection electrode (double platinum pin electrode),
- (7) is a titration vessel,
- (8) is an anolyte, and
- (9) is a rotor.

In this assay the following devices, reagents and experimental conditions can be used:

1. Apparatus

The specific apparatus used is the METTLER DO 337 Drying Oven coupled with the METTLER DL 37 KF Coulometer.

2. Reagents Used in the Titration cell

Hydranalo®—Coulomat AG, art. 34836 (in compartment A)

Hydranalo®—Coulomat CG, art. 34840 (in compartment C) (supplier Riedel-de-Haën, D-30918 Seelze, Germany)

3. Experimental Conditions

The experimental conditions used for determining the (free) water content in the matrix of the transdermal patches were:

Flow of air: 300 ml/min

Temperature of the furnace: 80° C.

Size of the patch sample: 20 cm$^2$

Time of exposure of sample to 80° C.: 15 minutes

The system can detect from 100 to 3000 μg of (free) water equivalent to a percentage of water in the matrix of the present invention ranging approximately from 0.1 to 2.5%.

With this system the content of (free) water in the matrix is determined, the amount of water adsorbed on or absorbed by the silicon dioxide cannot be determined thereby.

For each of the products according to the two examples five units have been tested and the results are shown below:

TABLE 1

Moisture content in Estradiol-NETA patches

| Product | 1 | C-2 |
|---|---|---|
| Moisture wt. -% | 0.15 | 0.85 |
| | 0.13 | 0.81 |
| | 0.18 | 0.72 |
| | 0.15 | 0.78 |
| | 0.16 | 0.75 |
| Average | 0.15 | 0.78 |
| SD | 0.0013 | 0.0507 |

A comparative study of the flux trough human cadaver skin, carried out with the modified Franz diffusion cell, is presented in the following tables and graphs. It can be seen that the systems of the present invention exhibit elevated skin fluxes of Estradiol and Norethindrone Acetate (NETA) compared to the reference system.

Table 2 and Table 3: in-vitro Release (Human Skin) of Estradiol and NETA

Cumulative mean value: release of Estradiol and NETA

Release of Estradiol (μg/cm$^2$, n=3)

| Product | 8 h | 24 h | 48 h | 72 h | flux. μg/cm$^2$/h |
|---|---|---|---|---|---|
| 1 | 0.310 | 1.319 | 2.412 | 2.932 | 0.049 s.d. ± 0.0071 |
| C-2 | 0.217 | 0.797 | 1.424 | 2.054 | 0.031 s.d. ± 0.0021 |

Release of NETA (μg/cm$^2$, n=3)

| Product | 8 h | 24 h | 48 h | 72 h | flux. μg/cm$^2$/h |
|---|---|---|---|---|---|
| 1 | 1.118 | 2.482 | 4.395 | 5.481 | 0.090 s.d. ± 0.0014 |
| C-2 | 0.359 | 1.352 | 2.512 | 3.870 | 0.054 s.d. ± 0.0020 |

What is claimed is:

1. A transdermal patch for the release of estradiol and at least one progestogen agent through the skin, comprising an outer backing foil, a matrix and a protective liner wherein:

(a) the estradiol and the progestogen agents (s) are present in the matrix in an supersaturated solution, (b) the matrix contains 1 to 4 wt % activated SiO$_2$, and (c) the matrix has a moisture content of less than 0.7% wt.-%.

2. A transdennal patch according to claim 1 wherein the matrix has moisture content of less than 0.5 wt.-%.

3. A transdennal patch according to claim 1 wherein the matrix contains 2.5 to 3.5 wt % SiO$_2$.

4. A transdermal patch according to claim 1 wherein the SiO$_2$ is activated by irradiation with an infrared souce.

5. A transdermal patch according to claim 1 which is free of penetration enhancers.

6. A transdermal patch according to claim 1 wherein the matrix comprises one, two or more pressure sensitive adhesive copolymers obtainable by radical copolymerization of:

2-ethylhexyl acrylate, hydroxyethyl acrylate, vinylacetate and glycidyl methacrylate, in Quantities of up to 0.5 wt.-%, based on the weight of the matrix.

7. A transdermal patch according to claim 6 wherein the monomers are used in the following amounts:

2-ethylhexyl acrylate is used in an amount of 44 to 80 wt.-%, hydroxyethyl acrylate is used in an amount of 2.5 to 9.7 wt.-%, vinylacetate is used in an amount of 8 to 48.2 wt.-%, and glycidyl methacrylate is used in an amount of 0.01 to 0.3 wt.-% all percentages being based on the weight of the matrix.

8. A transdermal patch according to claim 1 wherein the matrix has a thickness of 20 to 100 μm.

9. A transdermal patch according to claim 1, wherein the matrix has an estradiol content of 1 to 3 wt.-%.

10. A transdermal patch according to claim 1, wherein the matrix has a progestogen agent content of 2 to 12 wt.-%.

11. A transdermal patch according to claim 1 wherein the matrix has a content of other compounds of up to 4 wt. %.

12. A transdermal patch according to claim 1 wherein the progestogen agent is norethindrone acetate.

13. A transdermal patch according to claim 1 wherein:

the backing foil comprises a material impermeable to the drugs and to the adhesive copolymer(s);

a side of the backing foil not facing the matrix is lacquered; and the backing foil has a thickness of 10 to 50 μm.

14. A transdermal patch according to claim 1 wherein the patch comprises a removable protective liner, made of at least one foil of paper, polyester, polyethylene, polyethylene terephtalate, polypropylene or polyvinylchloride or mixtures thereof, having thickness of 50 to 200 μm; and being provided with a cut-off tag and a stamped profile ring.

15. A transdermal patch according to claim 1, having a circular or oval shape or a square shape with round edges, and a release area of 5 to 60 cm$^2$.

16. A transdermal patch according to claim 1, wherein it is sealed in a sachet comprising a humidity impermeable foil which is made of sheets of aluminum, paper, polyethylene, polyvinylchloride or ionomer foil.

17. A transdermal patch according to claim 16, wherein the sachet contains a desiccant taken from the group comprising silica gel, sodium sulfate, calcium sulfate, calcium carbonate dihydrate or a mixture thereof.

18. A process for the production of a transdermal patch according to claim 1 which includes the steps of:

a) providing estradiol and at least one progestogen agent which are mixed with a copolymer solution, b) adding silicon dioxide to the mixture, c) applying the mixture to a backing layer to form a laminate, d) applying the mixture at a temperature from 35 to 95° C., e) irradiating the laminate with IR-rays, and f) covering the laminate a protective liner.

19. A method of manufacture of a medicament for hormonal replacement therapy comprising the step of creating a transdermal patch in accordance with claim 1.

20. A transdermal patch according to claim 7 wherein:

2-ethylhexyl acrylate is in an amount of 48 to 75 wt.-%, hydroxyethyl acrylate is in an amount of 4.0 to 5.0 wt.-%, and glycidyl methacrylate is in an amount of 0.1 to 0.2 wt.-%.

21. A transdermal patch in accordance to claim 7 wherein:

2-ethythexyl acrylate is in an amount of 50 to 68 wt.-%.

22. A transdermal patch according to claim 9 wherein the estradiol content is 1.5 to 2.5 wt.-%.

23. A transdermal patch according to claim 9 wherein the estradiol content is 1.8 to 2.4 wt.-%.

24. A transdermal patch according to claim 10 wherein the progestogen agent content is 4 to 11 wt.-%.

25. A transdermal patch according to claim 10 wherein the progestogen agent content is 5 to 9 wt.-%.

26. A transdermal patch according to claim 13 wherein:

the backing foil is made from one or more materials selected froze group consisting of polyester, polyurethane, polyethylene, polyethylene terephtalate, polypropylene and polyvinyl chloride materials;

the side of the backing foil comprises epoxy resins or polyaminoamido resins containing opacifying agents; and the backing foil has a thickness of 12 to 30 $\mu$m.

27. A transdermal patch according to claim 14 wherein the patch comprises a removable protective liner that is coated with silicone or a fluropolymer on one or both sides, and has a thickness of 80 to 150 $\mu$m.

28. A transdermal patch according to claim 15 wherein the release area is 8 to 40 cm$^2$.

29. A transdermal patch according to claim 16 wherein the sachet comprises a multi-layered foil.

* * * * *

UNITED STATES PATENT AND TRADEMARK OFFICE
CERTIFICATE OF CORRECTION

PATENT NO. : 6,440,454 B1
DATED : August 27, 2002
INVENTOR(S) : Antonino Santoro and Lucio C. Rovati It is certified that error appears in the above-identified patent and that said Letters Patent is hereby corrected as shown below:

<u>Column 9,</u>
Line 59, remove "an";

<u>Column 10,</u>
Line 2, change "souce" to -- source --;
Line 36, remove "the";
Line 37, remove "the"; and <u>Column 11,</u>
Line 4, after "laminate" add -- with --.

Signed and Sealed this

Third Day of December, 2002

JAMES E. ROGAN
*Director of the United States Patent and Trademark Office*